(12) United States Patent
Norcini et al.

(10) Patent No.: US 9,765,006 B2
(45) Date of Patent: Sep. 19, 2017

(54) PROCESS FOR THE PREPARATION OF A PHENYLINDAN PHOTOINITIATOR

(71) Applicant: IGM RESINS ITALIA S.R.L., Milan (IT)

(72) Inventors: Gabriele Norcini, Comabbio (IT); Angelo Casiraghi, Milan (IT); Enzo Meneguzzo, Sesto Calende (IT); Giovanni Floridi, Novara (IT); Giuseppe Li Bassi, Gavirate (IT)

(73) Assignee: IGM RESINS ITALIA S.R.L., Milan (IT)

( * ) Notice: Subject to any disclaimer, the term of this patent is extended or adjusted under 35 U.S.C. 154(b) by 0 days.

(21) Appl. No.: 15/316,315

(22) PCT Filed: Jun. 8, 2015

(86) PCT No.: PCT/EP2015/062664
§ 371 (c)(1),
(2) Date: Dec. 5, 2016

(87) PCT Pub. No.: WO2015/189124
PCT Pub. Date: Dec. 17, 2015

(65) Prior Publication Data
US 2017/0152202 A1 Jun. 1, 2017

(30) Foreign Application Priority Data
Jun. 10, 2014 (IT) .............. VA2014A0018

(51) Int. Cl.
| | | |
|---|---|---|
| C07C 45/72 | (2006.01) | |
| C07C 45/63 | (2006.01) | |
| C07C 45/46 | (2006.01) | |
| C07C 45/64 | (2006.01) | |
| B01J 31/10 | (2006.01) | |

(52) U.S. Cl.
CPC .............. *C07C 45/72* (2013.01); *B01J 31/10* (2013.01); *C07C 45/46* (2013.01); *C07C 45/63* (2013.01); *C07C 45/64* (2013.01); *C07C 2102/08* (2013.01)

(58) Field of Classification Search
CPC .......... C07C 45/46; C07C 45/72; C07C 45/63
USPC ................................................. 568/316
See application file for complete search history.

(56) References Cited

U.S. PATENT DOCUMENTS

| | | |
|---|---|---|
| 4,987,159 A | 1/1991 | Li Bassi et al. |
| 2007/0161814 A1 | 7/2007 | Jendralla et al. |
| 2009/0018354 A1 | 1/2009 | End et al. |

FOREIGN PATENT DOCUMENTS

| | | |
|---|---|---|
| CN | 102603509 A | 7/2012 |
| EP | 0161463 B1 | 2/1989 |
| EP | 1389177 B1 | 10/2008 |
| EP | 1620382 B1 | 9/2013 |
| WO | WO2004/099111 A1 | 11/2004 |
| WO | WO2009/135895 A1 | 11/2009 |

OTHER PUBLICATIONS

Written Opinion of the International Searching Authority for International Parent Application No. PCT/EP2015/062664 mailed on Oct. 28, 2015.
International Search Report of International Parent Application No. PCT/EP2015/062664 mailed on Oct. 28, 2015.
Search Report of Italian Priority Application No. ITVA2014A0018 dated Feb. 20, 2015.
Song, Guo-Qiang et al. "Preparation and Properties of Difunctional Hydroxy Ketone as Photoinitiator", vol. 30, No. 8, Aug. 2013 (Aug. 2013), pp. 888-891.

*Primary Examiner* — Sikarl Witherspoon

(57) ABSTRACT

The present invention refers to a process for producing 5-[4-(2-hydroxy-2-methyl)-1-oxo-prop-1-yl]-3-[4-(2-hydroxy-2-methyl)-1-oxo-prop-1-yl-phenyl]-2,3-dihydro-1,1,3-trimethyl-1H-indene (dimer isomer 5) that comprises the acylation of cumene in the 4-position with an isobutyryl halide, followed by benzylic halogenation and dimerization (cyclization) of the resulting product.

10 Claims, No Drawings

PROCESS FOR THE PREPARATION OF A PHENYLINDAN PHOTOINITIATOR

RELATED APPLICATIONS

This application is the US national phase application of international application number PCT/EP2015/062664, filed 08 Jun. 2015, which designates the US and claims priority to Italian Application No. VA2014A000018 filed 10 Jun. 2014, the contents of each of which are hereby incorporated by reference as if set forth in their entireties.

TECHNICAL FIELD

The present invention refers to a process for producing a regioisomer of a phenylindan photoinitiator (5-[4-(2-hydroxy-2-methyl)-1-oxo-prop-1-yl]-3-[4-(2-hydroxy-2-methyl)-1-oxo-prop-1-yl-phenyl]-2,3-dihydro-1,1,3-trimethyl-1H-indene, dimer isomer 5), in solid and pure form.

BACKGROUND OF THE ART

The use of oligomeric photoinitiators in photopolymerisation has several advantages in comparison with the use of monomeric photoinitiators, such as lower migratability of the photoinitiator and reduced amount of volatile compounds derived from their photodecomposition. Those characteristics are important for the industrial use of the photoinitiator because they reduce the risk of contamination of the finished products.

Among the known oligomeric photoinitiators, the alpha-hydroxycarbonyl derivatives of oligomers of alpha-methylstyrene of formula A, wherein n is a number equal or greater than zero, are mostly appreciated in the field.

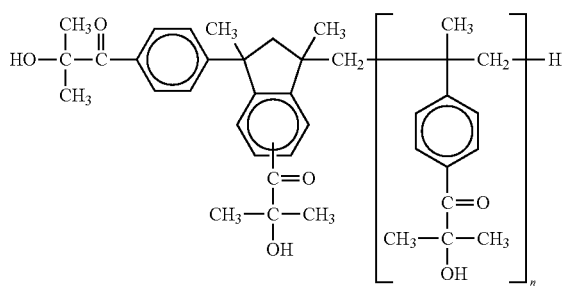

A

These photoinitiators are described in U.S. Pat. No. 4,987,159 and they are mainly constituted by mixtures of dimer and trimer isomers. At room temperature these mixtures of dimer and trimer isomers are highly viscous products that usually require pre-heating for easy handling.

As a consequence, solid mixtures of alpha hydroxycarbonyl derivatives of alpha-methylstyrene oligomers in powder form have been developed and are now highly appreciated photoinitators for photopolymerising acrylic systems.

Their composition and synthesis is reported in EP 1389177.

The solid mixtures of alpha hydroxycarbonyl derivatives of alpha-methylstyrene oligomers of EP 1389177 contain about 90-98% of two dimer isomers: 5-[4-(2-hydroxy-2-methyl)-1-oxo-prop-1-yl]-3-[4-(2-hydroxy-2-methyl)-1-oxo-prop-1-yl-phenyl]-2,3-dihydro-1,1,3-trimethyl-1H-indene (dimer isomer 5) and 6-[4-(2-hydroxy-2-methyl)-1-oxo-prop-1-yl]-3-[4-(2-hydroxy-2-methyl)-1-oxo-prop-1-yl-phenyl]-2,3-dihydro-1,1,3-trimethyl-1H-indene (dimer isomer 6).

Dimer isomer 5 is the compound of formula V:

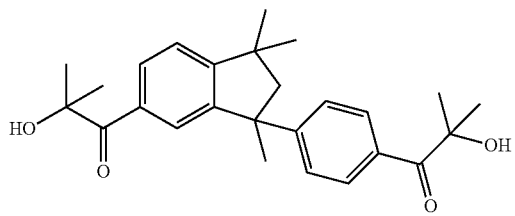

V

Dimer isomer 6 is the compound of formula VI

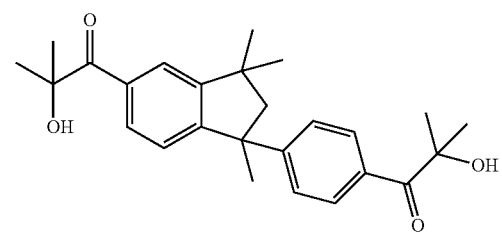

VI

The process of EP 1389177 provides these solid mixtures through controlled crystallization of the high viscosity mixtures of alpha-hydroxycarbonyl derivatives of oligomers of alpha-methylstyrene, whose synthesis is described, for instance, in U.S. Pat. No. 4,987,159.

Both dimer isomers are active as photoinitiators, but dimer isomer 5 is more reactive in photopolymerization than dimer isomer 6, as it is also reported in EP 1389177.

One of the advantage of the controlled crystallization of EP 1389177 is that it provides solid mixtures of alpha hydroxycarbonyl derivatives of alpha-methylstyrene oligomers that are enriched in dimer isomer 5.

A process for the preparation of a crystalline mixture of dimer isomer V and VI is also described in EP 1620382. The process uses 1,1,3-trimethyl-1-phenylindan as the starting product and may be adapted for the preparation of the individual dimer isomer V through separation of one of the intermediates.

Both the process of EP 1389177 and the process of EP 1620382 prepare alpha-hydroxycarbonyl derivatives of alpha-methylstyrene dimers by acylation of alpha-methylstyrene oligomers or dimers. Due to the fact that acylation occurs both in the 5- and 6-positions, mixtures of 5- and 6-isomers are always obtained and the preparation of dimer isomer 5 in enriched or isolated form implies the discharge or separate use of the less reactive dimer isomer 6.

As a consequence it would be highly desirable to design a short, efficient and isomer 6-free synthesis of dimer isomer 5 which also dispenses with costly and inconvenient purification steps and provides the product in solid and pure form.

It has now been found that this objective is achieved by a process that comprises the acylation of cumene in the 4-position with an isobutyryl halide, followed by benzylic halogenation and dimerization (cyclization) of the resulting product.

SUMMARY OF THE INVENTION

Accordingly, the main object of the present disclosure is a process for the preparation of 5-[4-(2-hydroxy-2-methyl)-1-oxo-prop-1-yl]-3-[4-(2-hydroxy-2-methyl)-1-oxo-prop-1-yl-phenyl]-2,3-dihydro-1,1,3-trimethyl-1H-indene (dimer isomer 5) comprising the following steps:

i. cumene is acylated with a compound of formula Ia, where $X_0$ is Cl or Br and $X_1$ is Cl or Br to obtain a compound of formula IIa and the compound of formula IIa is halogenated to obtain a compound of formula IIIa, where $X_1$ and $X_2$ are independently Cl or Br; or cumene is acylated with a compound of formula Ib, where $X_0$ is Cl or Br to obtain a compound of formula IIb and the compound of formula IIb is halogenated to obtain a compound of formula IIIb, where $X_1$ is Cl or Br, according to the following schemes:

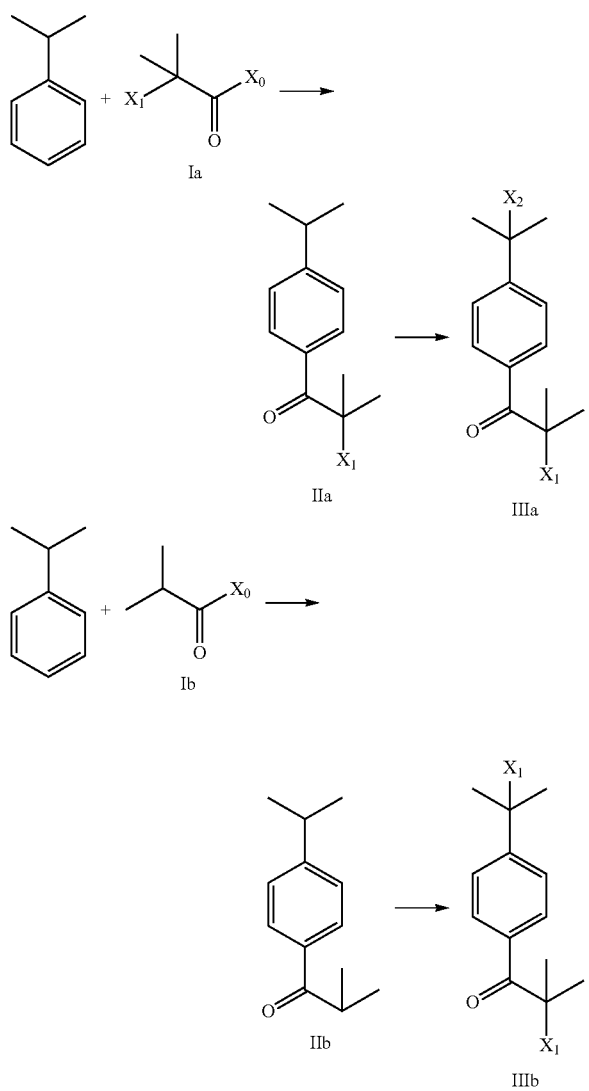

ii. the compound of formula IIIa or IIIb is cyclized with an acid catalyst to obtain the compound of formula IV, in which $X_1$, is Cl or Br, according to the following scheme:

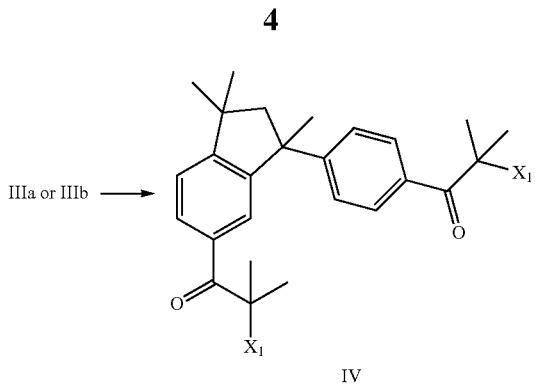

iii. the compound of formula IV is hydrolysed to obtain the compound of formula V (dimer isomer 5):

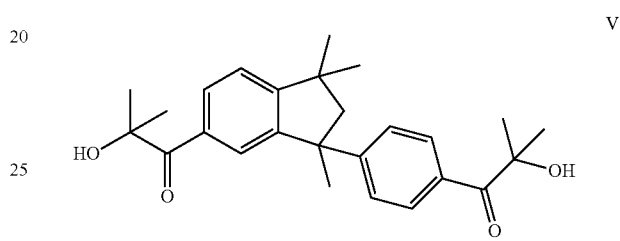

DETAILED DESCRIPTION OF THE INVENTION

The acylation of cumene with a compound of formula Ia or Ib is a Friedel Craft acylation. The specific substrate (cumene) renders the acylation highly regioselective, and provides almost exclusively para-substituted cumene derivatives (selectivity about 98% as determined by H-NMR).

Compounds IIIa and IIIb are therefore easily obtained from cumene in few steps with very high selectivity.

The compounds of formula Ia and Ib are commercially available acyl halides. The preferred compounds of formula Ia are alpha-chloroisobutyrylchloride and alpha-bromoisobutyrylbromide; the preferred compound of formula Ib is isobutyryl chloride.

In step i., cumene and the acyl halide are preferably mixed and reacted in the absence of a solvent, or dissolved in an organic solvent. Any solvent which is inert in the acylation conditions may be used. Examples of solvents that can be used are dichloromethane, chlorobenzene, ethylenechloride, 1,2-dichlorobenzene, nitromethane, tetrachlorethane; the preferred solvents are dichloromethane and chlorobenzene.

From 1.50 to 1.10 moles of the acyl halide, preferably from 1.10 to 1.05, per mole of cumene are used in step i.

The acylation of step i. is typically carried out by adding from 1.5 to 0.1 moles, per mole of cumene, of a Lewis acid, such as $AlCl_3$, $FeCl_3$, $TiCl_4$, $BF_3$ or $SnCl_4$, preferably of $AlCl_3$, preferably at temperature between −20° and +20° C., more preferably between −10° and 10° C. The work up of the reaction is made as usual in the art, by hydrolyzing the reaction mixture with water and separating the resulting product, possibly dissolved in the solvent.

Quantitative yields are obtained in the acylation.

The halogenation of the compound of formula IIa is a benzylic halogenation that can be performed as described in US 2007/0161814, by reaction of the compound of formula IIa with N-bromosuccinimide with illumination using a sunlight lamp or UV lamp, or in presence of catalytic amounts of dibenzoyl peroxide or 2,2'-azoisobutyronitrile (AIBN), or by reaction with sulfuryl chloride, chlorine or bromine, or with t-butyl-ipochlorite under free radical conditions (illumination or presence of catalytic amounts of dibenzoyl peroxide or AIBN). Halogenation may be carried out in the same halogenated solvent that has been used in the acylation of step i., if any, or in another compatible solvent, such as methylene chloride, chlorobenzene, 1,2-dichlorobenzene or other halogenated solvent.

Alternatively, when in step i. the acylation is performed with a compound of formula Ib, the halogenation of the resulting compound of formula IIb can be performed in one step both in the benzylic and alpha-keto position (enol halogenation) by using chlorine, or bromine or sulfuryl chloride, as reported in EP 161463 for stage (C).

In step ii. the compound of formula IIIa or IIIb is cyclized (dimerized) with an acid catalyst to obtain a compound of formula IV, where $X_1$ is Cl or Br.

The acid catalyst can be an inorganic or an organic strong acid, such a a sulfonic of phosphonic acid, or a Lewis Acid. The preferred acid catalysts are acid clays, ion exchange resins with sulfonic groups in acid form, $C_6$-$C_{18}$ arylsulphonic acids and trifluoromethanesulphonic acid. More preferably the acid catalyst is a ion exchange resins with sulfonic groups in acid form or an inorganic acid. The reaction can be carried out in solvents or without solvents at a temperature from 40 to 140° C.

In step iii. the compound of formula IV is hydrolysed. The compound of formula IV may be reacted with an alkali metal alkoxide, preferably with sodium methylate in methanol, and hydrolysed with an aqueous acid to give the compound of formula V (dimer 5), as reported by way of example in EP 0 161 463 (stage (D) and stage (E)) and in U.S. Pat. No. 4,987,159 (Example 4); alternatively, the compound of formula IV may be directly hydrolised with an alkali metal hydroxide, by way of example with NaOH 30 wt % in methanol, as described in WO 2004/099111 (Example 1.3), or with NaOH 30 wt % in water, to give the compound of formula V.

The compound of formula V may be obtained in solid and pure form by crystallization from toluene, i-propanol, ethyl acetate or other solvent, as reported, by way of example, in EP 1389177.

EXAMPLES

Example 1

Synthesis of 2-chloro-1-(4-isopropylphenyl)-2-methylpropan-1-one (compound formula IIa)

A solution of cumene (20.0 g, 0.165 moles) and alpha-chloro-i-butyrylchloride (24.7 g, 0.173 moles) in methylene chloride (250 g) was stirred under nitrogen at 5° C. Aluminum chloride (24.2 g, 0.182 moles) was added in portions to the solution in 90 minutes at the same temperature. After one additional hour under stirring the solution was poured in iced water under stirring. The organic phase was washed with water and the methylene chloride was distilled off under vacuum obtaining 38.0 g of clear oil. Yield: quantitative.

$H_1$NMR (CDCl$_3$, δ ppm): 1.26(d, 6H), 1.85(s, 6H), 2.95 (m, 1H), 7.29(d, 2H), 8.13(d, 2H).

Example 2

Synthesis of 2-chloro-1-(4-(2-chloropropan-2-yl) phenyl)-2-methylpropan-1-one (compound formula IIIa)

2-chloro-1-(4-isopropylphenyl)-2-methylpropan-1-one (10.0 g, 0.045 moles) was dissolved in chlorobenzene (73 g) and de-oxygenated by nitrogen under stirring at room temperature. Then the solution was cooled at −10° C. and t-butyl hypochlorite (7.24 g, 0.067 moles prepared as described in Organic Syntheses, Coll. Vol. 5, 184 (1973)) was added in one portion obtaining a yellow solution. The stirred solution was illuminated with a 300 W Osram Ultra Vitalux lamp, until the solution was discolored and the temperature raised to 20° C. After cooling to room temperature, the solvent was distilled off under vacuum obtaining 11 g of clear oil. Yield: quantitative.

$H_1$NMR (CDCl$_3$, δ ppm): 1.86(s, 6H), 1.95(s, 6H), 7.15 (d, 2H), 8.13(d, 2H).

Example 3

Synthesis of 5-(2-chloro-2-methyl-1-oxo-prop-1-yl)-3-(4-(2-chloro-2-methyl-1-oxo-prop-1-yl)phenyl)-2,3-dihydro-1,1,3-trimethyl-1H-indene (compound formula IV)

2-chloro-1-(4-(2-chloropropan-2-yl)phenyl)-2-methylpropan-1-one (8.30 g, 0.032 moles) was heated at 135° C. under stirring in presence of 1.50 g of catalyst Amberlyst 15. After 5 hours the reaction was complete (TLC SiO$_2$, toluene). After cooling the solid mass was dissolved in methylene chloride and the catalyst was filtered off. After evaporation of the solvent under vacuum, were obtained 5.89 g (82.5% yield) of an oil that solidify after standing. A sample was crystallized in toluene obtaining a white solid mp 139°-140° C. Yield: quantitative.

$H_1$NMR (CDCl$_3$, δ ppm): 1.03(s, 3H), 1.38(s, 3H), 1.73(s, 3H), 1.86(m, 12H), 2.26(d, 1H), 2.47(d, 1H), 7.25(m, 3H), 7.92(s, 1H), 8.07(d, 2H), 8.18(d,1H).

Example 4

Synthesis of 5-[4-(2-hydroxy-2-methyl)-1-oxo-prop-1-yl]-3-[4-(2-hydroxy-2-methyl)-1-oxo-prop-1-yl-phenyl]-2,3-dihydro-1,1,3-trimethyl-1H-indene (dimer isomer 5, compound of formula V)

5-(2-chloro-2-methyl-1-oxo-prop-1-yl)-3-(4-(2-chloro-2-methyl-1-oxo-prop-1-yl)phenyl)-2,3-dihydro-1,1,3-trimethyl-1H-indene (5.2 g, 0.011 moles) was dissolved in methylene chloride (30 g) and a 30% water solution of NaOH (7.30 g, 0.055 moles) were added. The mixture was heated at reflux in presence of tetrabutylammonium bromide (0.10 g). After 8 hours the reaction was complete (TLC SiO$_2$, toluene: ethylacetate 8:2). The organic phase was washed with water and dried over sodium sulfate, after evaporation of the solvent were obtained 4.5 g of compound I as an oil that solidify after standing. A sample was crystallized in toluene obtaining a white powder, mp117-118° C. Yield: almost quantitative $H_1$NMR (CDCl$_3$, δ ppm): 1.04(s, 3H), 1.37(s, 3H), 1.61 (m, 12H), 1.73(s, 3H), 2.25(d, 1H), 2.46(d, 1H), 3.90-4.10 (bs, 2 OH), 7.25(m, 3H), 7.80(s, 1H), 7.92(d, 2H), 8.00(d, 1H).

The invention claimed is:
1. Process for the preparation of 5-[4-(2-hydroxy-2-methyl)-1-oxo-prop-1-yl]-3-[4-(2-hydroxy-2-methyl)-1-oxo-prop-1-yl-phenyl]-2,3-dihydro-1,1,3-trimethyl-1H-indene (dimer isomer 5) comprising the following steps:
  i. cumene is acylated with a compound of formula Ia, where $X_0$ is Cl or Br and $X_1$ is Cl or Br to obtain a compound of formula IIa and the compound of formula IIa is halogenated to obtain a compound of formula IIIa, where $X_1$ and $X_2$ are independently Cl or Br; or cumene is acylated with a compound of formula Ib, where $X_0$ is Cl or Br to obtain a compound of formula IIb and the compound of formula IIb is halogenated to obtain a compound of formula IIIb, where $X_1$ is Cl or Br, according to the following schemes:

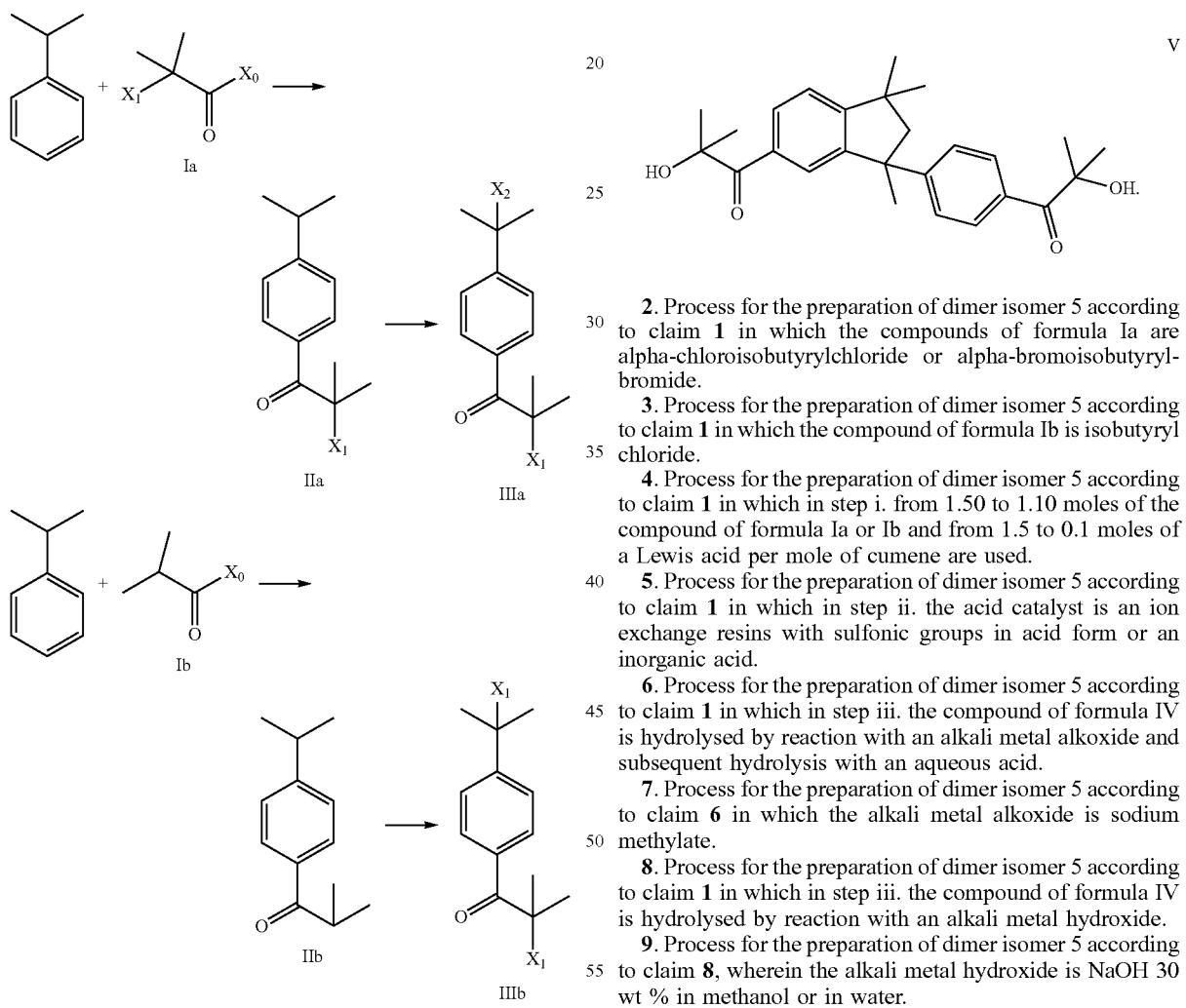

ii. the compound of formula IIIa or IIIb is cyclized with an acid catalyst to obtain the compound of formula IV, in which $X_1$ is Cl or Br, according to the following scheme:

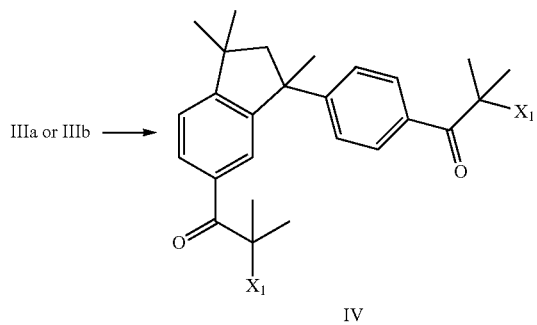

iii. the compound of formula IV is hydrolysed to obtain the compound of formula V (dimer isomer 5):

2. Process for the preparation of dimer isomer 5 according to claim 1 in which the compounds of formula Ia are alpha-chloroisobutyrylchloride or alpha-bromoisobutyrylbromide.
3. Process for the preparation of dimer isomer 5 according to claim 1 in which the compound of formula Ib is isobutyryl chloride.
4. Process for the preparation of dimer isomer 5 according to claim 1 in which in step i. from 1.50 to 1.10 moles of the compound of formula Ia or Ib and from 1.5 to 0.1 moles of a Lewis acid per mole of cumene are used.
5. Process for the preparation of dimer isomer 5 according to claim 1 in which in step ii. the acid catalyst is an ion exchange resins with sulfonic groups in acid form or an inorganic acid.
6. Process for the preparation of dimer isomer 5 according to claim 1 in which in step iii. the compound of formula IV is hydrolysed by reaction with an alkali metal alkoxide and subsequent hydrolysis with an aqueous acid.
7. Process for the preparation of dimer isomer 5 according to claim 6 in which the alkali metal alkoxide is sodium methylate.
8. Process for the preparation of dimer isomer 5 according to claim 1 in which in step iii. the compound of formula IV is hydrolysed by reaction with an alkali metal hydroxide.
9. Process for the preparation of dimer isomer 5 according to claim 8, wherein the alkali metal hydroxide is NaOH 30 wt % in methanol or in water.
10. Process for the preparation of dimer isomer 5 according to claim 1, wherein the compound of formula V is obtained in solid and pure form by crystallization after completing step iii.

* * * * *